(12) United States Patent
Buttle

(10) Patent No.: US 7,215,117 B2
(45) Date of Patent: May 8, 2007

(54) MEASUREMENT WITH A MAGNETIC FIELD

(75) Inventor: David John Buttle, Wantage (GB)

(73) Assignee: ESR Technology Ltd., Warrington (GB)

( * ) Notice: Subject to any disclaimer, the term of this patent is extended or adjusted under 35 U.S.C. 154(b) by 54 days.

(21) Appl. No.: 10/492,135

(22) PCT Filed: Oct. 7, 2002

(86) PCT No.: PCT/GB02/04531

§ 371 (c)(1), (2), (4) Date: Apr. 7, 2004

(87) PCT Pub. No.: WO03/034054

PCT Pub. Date: Apr. 24, 2003

(65) Prior Publication Data

US 2005/0001612 A1 Jan. 6, 2005

(30) Foreign Application Priority Data

Oct. 17, 2001 (GB) ................................ 0124910.1
Apr. 19, 2002 (GB) ................................ 0208960.5

(51) Int. Cl.
*G01B 7/24* (2006.01)
*G01N 27/72* (2006.01)

(52) U.S. Cl. ........................................ 324/209; 324/233

(58) Field of Classification Search ................ 324/228, 324/233, 229, 230, 232, 209; 73/772, 773, 73/779, 794, 801, 862.69
See application file for complete search history.

(56) References Cited

U.S. PATENT DOCUMENTS 3,358,225 A * 12/1967 Peugeot ....................... 324/225

(Continued)

FOREIGN PATENT DOCUMENTS

| EP | 0282930 | | 9/1988 |
|---|---|---|---|
| EP | 0631147 A1 | * | 6/1994 |
| EP | 0631147 | | 12/1994 |

OTHER PUBLICATIONS

Probe Modelling to Enable Biaxial Stress Measurement Depth Profiling, D.J. Buttle and C.C. Holt, Nondestructive Testing of Materials, IOS Press, 1995.*

(Continued)

*Primary Examiner*—Edward Lefkowitz
*Assistant Examiner*—David M. Schindler
(74) *Attorney, Agent, or Firm*—William H. Holt

(57) ABSTRACT

Material properties such as stress in a ferromagnetic material may be measured using an electromagnetic probe. While generating an alternating magnetic field in the object, and sensing the resulting magnetic field with a sensor, the signals from the magnetic sensor may be resolved into in-phase and quadrature components. The signals are affected by both geometrical parameters such as lift-off and by material properties, but these influences may be separated by mapping the in-phase and quadrature components directly into material property and lift-off components, and hence a material property and/or the lift-off may be determined. The mapping may be represented in the impedance plane as two sets of contours representing signal variation with lift-off (A) (for different values of stress) and signal variation with stress (B) (for different values of lift-off), the contours of both sets (A, B) being curved. The stress contours (B) intersect any one liftoff contour (A) at a constant angle. Hence calibration measurements taken along a few contours of each set enable the positions of the other contours of each set to be determined.

5 Claims, 2 Drawing Sheets

U.S. PATENT DOCUMENTS

| | | | | |
|---|---|---|---|---|
| 3,742,357 | A | * | 6/1973 | Kubo et al. .................. 324/209 |
| 4,727,322 | A | | 2/1988 | Lonchampt |
| 4,755,753 | A | * | 7/1988 | Chern ........................ 324/237 |
| 5,293,117 | A | * | 3/1994 | Hwang ....................... 324/220 |
| 5,341,678 | A | * | 8/1994 | Kervinen ................... 73/150 R |
| 5,541,510 | A | * | 7/1996 | Danielson ................... 324/233 |
| 5,828,211 | A | | 10/1998 | Scruby et al. |
| 5,963,031 | A | * | 10/1999 | de Halleux et al. ......... 324/230 |
| 6,188,218 | B1 | * | 2/2001 | Goldfine et al. ............ 324/243 |

OTHER PUBLICATIONS

Patent Abstracts of Japan: Abstract of Publication No. 63311165; Publication Date Dec. 19, 1988; Kawasaki Steel Corp.

\* cited by examiner

MEASUREMENT WITH A MAGNETIC FIELD

BACKGROUND OF THE INVENTION

This invention relates to a method and apparatus in which an electromagnetic probe is used to measure material properties in a ferromagnetic material, for example stress, or to measure the separation of the probe from the surface of such a material.

The stresses in structures such as rails, bridges and pipelines, complex mechanisms such as vehicles and machinery, or simple devices such as struts, cables or bearings arise from various causes including changes of temperature, and the loads and pressures due to use. There may also be residual stresses arising from the fabrication of the structure or device, and any bending that the structure or device was subjected to during construction; the residual stresses arising from fabrication will also be affected by any stress-relieving heat treatment. In some situations (such as pipelines) the principal stress directions can be expected to be in particular directions (circumferential and longitudinal), whereas in other situations the stress directions are also unknown. A variety of magnetic techniques are known to have some sensitivity to stress, although magnetic measurements are usually also affected by other material properties such as microstructure. A way of measuring stress in a steel plate is described in GB 2 278 450, this method using a probe containing an electromagnetic core to generate an alternating magnetic field in the plate, and then combining measurements from two sensors, one being a measure of stress-induced magnetic anisotropy, and the other being a measure of directional effective permeability (DEP). The probe is gradually turned around so the magnetic field has a plurality of different orientations in the plate, and these measurements are taken at each such orientation. The DEP signals are affected not only by stress, but also by the lift-off from the surface (i.e. the gap or separation between the probe and the surface), and so must be corrected for lift-off.

According to the present invention there is provided a method for measuring biaxial stresses in an object of ferromagnetic material using at least one probe, the or each probe comprising an electromagnet means and a magnetic sensor arranged for sensing a magnetic field due to the electromagnet means; the method comprising detecting signals from the magnetic sensor and resolving them into first and second components that are orthogonal in phase, and mapping the first and second components directly into apparent stress and liftoff components; taking such measurements with the one said probe oriented with two principal stress axes of the object, and deducing two corresponding values of apparent uniaxial stress; and hence deducing the true biaxial stresses in said object.

The mapping requires a preliminary calibration, with a specimen of the material, to determine how the first and second components of the signal vary with lift-off (at a constant stress) and vary with stress (at a constant lift-off), and deducing from the calibration measurements the applicable mapping for any stress and any lift-off. The signals from the sensor are at the frequency of the alternating field, and the components may be the components in phase with the current supplied to the electromagnet means, and the component in quadrature to that. The mapping may be represented in the impedance plane (i.e. on a graph of quadrature component against in-phase component) as two sets of contours representing signal variation with lift-off (for different values of stress) and signal variation with stress (for different values of lift-off), the contours of both sets being curved. The contours or lines of one set intersect those of the other set at non-orthogonal angles. The angles at which the contours for constant lift-off (varying stress) intersect any one contour for constant stress (varying lift-off) are constant along that contour. However the angles of intersection of different lift-off lines with any one stress line are different: the angle of intersection at a fixed lift-off varies slightly with stress. Hence measurements taken along a few contours of each set enable the positions of the other contours of each set to be determined.

Surprisingly this simple mapping has been found to give an accurate representation of the variation of the signals with material property (e.g. stress or microstructure); more surprisingly it enables these variations to be distinguished unambiguously from variations arising from lift-off or other geometrical variations such as surface texture or curvature. It may perhaps be presumed that material property changes cause changes in the permeability of the steel in the magnetic circuit and these have both inductive and resistive (lossy) components, whereas geometrical changes such as lift-off change the amount of air in the magnetic circuit, in which energy dissipation by eddy currents cannot occur, so this of itself would be purely inductive (non-lossy). Where the object has a coating of a non ferromagnetic material (such as a paint, or a ceramic), this coating will separate the probe from the surface, so the lift-off measurement may indicate its thickness.

Preferably the electromagnet means comprises an electromagnetic core and two spaced apart electromagnetic poles, and the magnetic sensor is preferably arranged to sense the reluctance of that part of the magnetic circuit between the poles of the electromagnet means. It is also desirable to arrange for such measurements to be taken with a plurality of different orientations of the magnetic field, at a single location on the object. This may be achieved using a single probe that is rotated at that location, measurements being taken with different orientations of the probe, or using an array of probes of different orientations that are successively moved to that location. In either case, the sensor or sensors provide a measure of the permeability of the material through which the flux passes between the poles, and so provide a signal indicative of the effective permeability of the material; the corresponding measurements at different probe orientations at a location on the object hence indicate the effective permeability in different directions. The signals from this sensor may be referred to as a reluctance, or 'flux linkage', signal.

The probe, or at least some of the probes, may also include a second magnetic sensor between the two poles and arranged to sense magnetic flux density perpendicular to the direction of the free space magnetic field between the poles. This second sensor would detect no signal if the material were exactly isotropic; however stress induces anisotropy into the magnetic properties of the material, and so the signals received by the second sensor are a measure of this stress-induced magnetic anisotropy or 'flux rotation'. The variations in the flux rotation signals at different probe orientations, at a location on the object, enable the directions of the principal stress axes to be accurately determined. The flux rotation signals can also be related to the stress.

The flux linkage signal from the or each probe is preferably backed-off, i.e. processed by first subtracting a signal equal to the signal from that sensor with the probe adjacent to a stress-free location. The backed-off signal is then amplified so the small changes in the flux linkage signal due to stress are easier to detect. This backing off is performed after resolving into in-phase and quadrature components but before performing the mapping. Preferably the signals from the or each probe are digitized initially, and the backing-off and resolution are performed by analysis of the digital signals.

To achieve penetration below the surface of the ferromagnetic object it is desirable to operate at alternating frequencies less than 200 Hz, for example between 5 Hz and 100 Hz (which in mild steel provide penetrations of about 5 mm and 1 mm respectively). In other situations, where such depth of penetration is not required, higher frequencies can be used, for example up to 150 kHz for a penetration of only about 15 μm. The depth of penetration may be represented by the skin depth, $\delta = 1/\sqrt{(\pi\mu_o\mu_r fk)}$, where $\mu_o$ is the permeability of free space, $\mu_r$ is the relative permeability of the material, k is its electrical conductivity, and f is the frequency. The frequency should be such that the skin depth is much less than the thickness of the object.

Generally, the more different probe orientations are used for taking measurements the more accurate the determination of stress levels and principal axes can be. In many cases the principal stress axes can be assumed to be aligned in particular directions—axial and circumferential directions in the case of a pipe, for example—so that the signal maxima for flux linkage signals would be expected to be along these directions, and the signal maximum for flux rotation signals would be along the bisection angles between these directions.

The probe, or at least some of the probes, may also include a third magnetic sensor (a 'flux leakage' sensor) between the poles and arranged to sense magnetic flux density parallel to the free space magnetic field. This third sensor will detect any flux leakage, this being influenced by changes in material properties, lift-off, and cracks. As with the flux-linkage sensor, measurements at a location are preferably made at different probe orientations.

BRIEF DESCRIPTION OF THE DRAWINGS

The invention will now be further and more particularly described, by way of example only, and with reference to the accompanying drawings, in which.

DETAILED DESCRIPTION OF THE INVENTION

Figure 1:
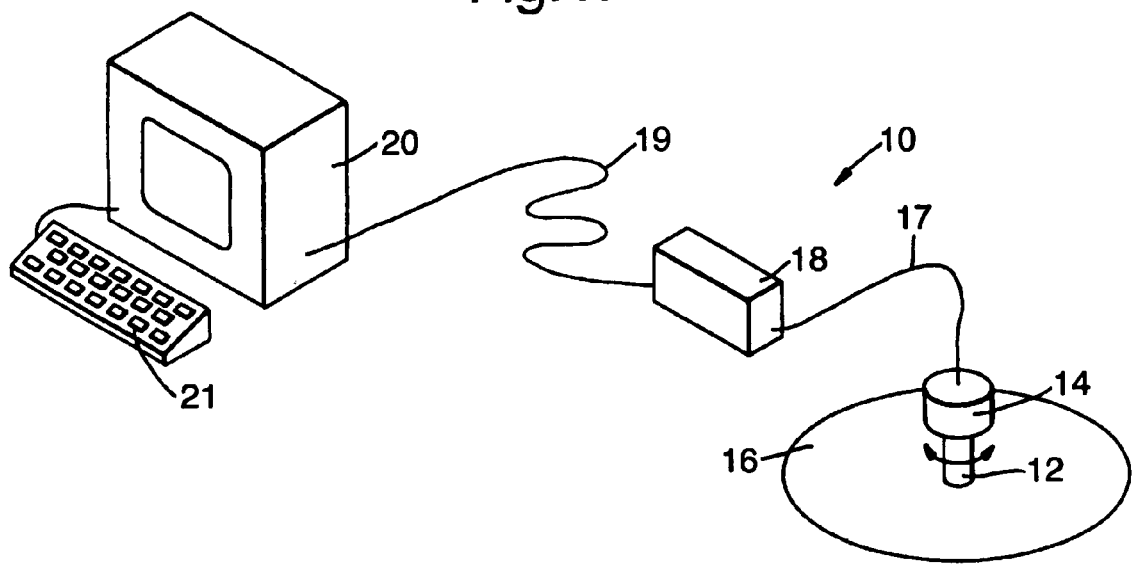
FIG. 1 shows a diagrammatic view of an apparatus for measuring stress or lift-off.

Referring to FIG. 1, an apparatus 10 for measuring stress and/or lift-off includes a sensor probe 12 comprising sensors for both flux linkage and flux rotation, the probe 12 being attached to an electric motor 14 which can be held by an operator, so the motor 14 can turn the probe 12 with one end adjacent to a surface of a steel object 16 in which the stress is to be determined. The sensor probe 12 and motor 14 are connected by a 2 m long umbilical cable 17 to a signal conditioning/probe driver unit 18. The unit 18 is connected by a long umbilical cable 19 (which may for example be up to 300 m long) to an interface unit within a microcomputer 20, which has a keyboard 21. Operation of the apparatus 10 is controlled by software in the microcomputer 20.

The interface unit within the microcomputer 20 generates sine and cosine functions at an angular frequency selectable by software, and buffers the sine waveform for transmission to the unit 18 for driving the probe 12. The amplitude of the transmitted waveform is also selectable by software. It also provides signals to control the motor 14 and hence the angular position of the probe 12. The interface unit also provides control signals to the unit 18 to select which of the signals available from the probe 12 is to be transmitted for analysis. It demodulates the selected input signal (flux linkage or flux rotation) to derive its in-phase and quadrature components, filters the demodulated signal to remove high frequency components and to reduce noise, and converts the analogue signals to digital form for input to the computer 20. It also detects the angular position of the probe 12 from signals provided by a position encoder (not shown) on the motor 14.

The long umbilical cable 19 incorporates a coaxial cable to transmit the selected signal, and wires to control which signal is selected, to control the motor 14, to transmit signals from the position encoder, to transmit the sinusoidal waveform, and to convey electrical power. The unit 18 converts the drive waveform from a voltage to a current drive for the probe 12; buffers and amplifies the signals from the probe 12; and selects which signal is to be transmitted to the microcomputer 20. It also buffers the signals from the position encoder for transmission, and drives the motor 14 in response to control signals.

Figure 2:
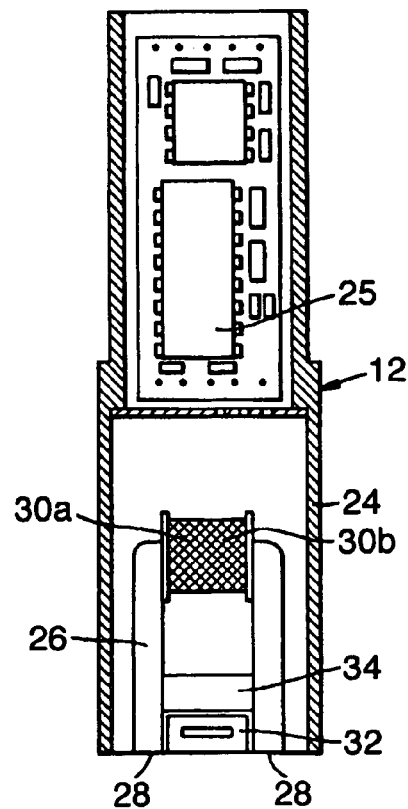
FIG. 2 shows a longitudinal sectional view of a probe for use in the apparatus of FIG. 1.

Referring now to FIG. 2, the probe 12 is shown detached from the motor 14, in longitudinal section although with the internal components shown in elevation (the connecting wires within the probe 12 are not shown). The probe 12 comprises a cylindrical brass casing 24 of external diameter 16.5 mm and of overall height 60 mm, the upper half being of reduced diameter whereby the probe 12 is attached to the motor 14. The upper half of the casing 24 encloses a head amplifier 25. The lower half encloses a U-core 26 of laminated mu-metal (a high permeability nickel/iron/copper alloy) whose poles 28 are separated by a gap 7.5 mm wide, and are each of width 2.5 mm, and of thickness 10 mm (out of the plane of the figure). The poles 28 are in the plane of the lower end of the casing 24, which is open. Around the upper end of the U-core 26 is a former on which are wound two superimposed coils 30. One coil 30a (which has 200 turns) is supplied with the sinusoidal drive current from the unit 18; the other coil 30b (which has 70 turns) provides flux linkage signals. Between the two poles 28 is a former on which is wound a 1670-turn rectangular coil 32, about 4 mm high and 6 mm wide, and 6 mm-square as seen from below, the windings lying parallel to the plane of the figure so the longitudinal axis of the coil 32 is perpendicular to the line between the centres of the poles 28. The coil 32 is supported by a support plate 34 fixed between the arms of the U-core 26 so the lower face of the coil 32 is in the plane of the poles 28. The coil 32 provides the flux rotation signals. The signals from the coils 30b and 32 are amplified by the head amplifier 25 before transmission to the unit 18.

On the same former as the coil 32 there may also be wound a 200-turn rectangular coil whose windings are perpendicular to the plane of the figure so the axis of the coil is parallel to the line between the centres of the poles. This coil would provide flux leakage signals. Alternatively such a flux leakage coil may be provided somewhat further from the surface, for example above the support plate 34.

In operation of the system 10, the motor 14 is supported so the lower end of the probe 12 is adjacent to the surface of the object 16 and the longitudinal axis of the probe 12 is normal to the surface. An alternating current of the desired frequency and amplitude is supplied to the drive coil 30a, so the magnetic field in the object 16 oscillates about zero with an amplitude much less than saturation. The probe 12 is first placed adjacent to a region of the object 12 where the stresses are negligible. The in-phase and quadrature components of the flux linkage signal (i.e. the component in phase with the drive current, and the component at 90° to the drive current) received by the microcomputer 20 are each backed off to zero, and the backing off values are then fixed. During all subsequent measurements the flux linkage signal components are backed off by these same amounts (i.e. subtracting a signal equal to the component observed when in a stress-free location).

Measurements can be taken by placing the probe 12 adjacent to a region in which material properties such as stress are to be measured. The orientation of the line joining the centres of the poles 28 (referred to as the orientation of the probe 12) is noted relative to a fixed direction on the surface. The motor 14 is then energized to rotate the probe 12, for example in a step-wise fashion 10° at a time through a total angle of 360°. At each orientation of the probe 12 the quadrature flux rotation signal is measured, and the flux linkage components are measured (and backed off). These measurements may be made at different frequencies, for example with a drive current frequency of 68 Hz when measuring flux rotation, and at a frequency of 300 Hz when measuring flux linkage. More typically the drive current frequency would be the same when measuring both parameters.

It will be appreciated that the signal analysis procedure of the invention is applicable with many different probes. The probe 12 might for example be modified by using a U-core 26 of a different material such as silicon iron (which can provide higher magnetic fields), or indeed the drive coil might be air-cored.

The probe might be of a different shape or size, for example for inspecting surface stress in a small bearing it may be appropriate to use a probe of diameter as small as 3 mm, and to operate at a higher frequency such as 100 kHz, while for inspecting internal stresses in a large steel pipe it may be appropriate to use a probe of diameter say 75 mm.

The flux rotation signals vary sinusoidally with probe orientation, so the orientation at which they have their maxima and minima can be determined. The directions midway between these two orientations are the directions of the principal stress axes. Measurements of the flux rotation signals are therefore useful if the principal stress directions are unknown. The flux linkage and flux leakage signals also vary sinusoidally with probe orientation (in antiphase with each other) and the values are observed at the principal stress directions. If the principal stress directions are already known, then the probe 12 might instead be merely oriented to those directions, and the flux linkage measurements made; no rotation of the probe 12 would be necessary.

Figure 3:
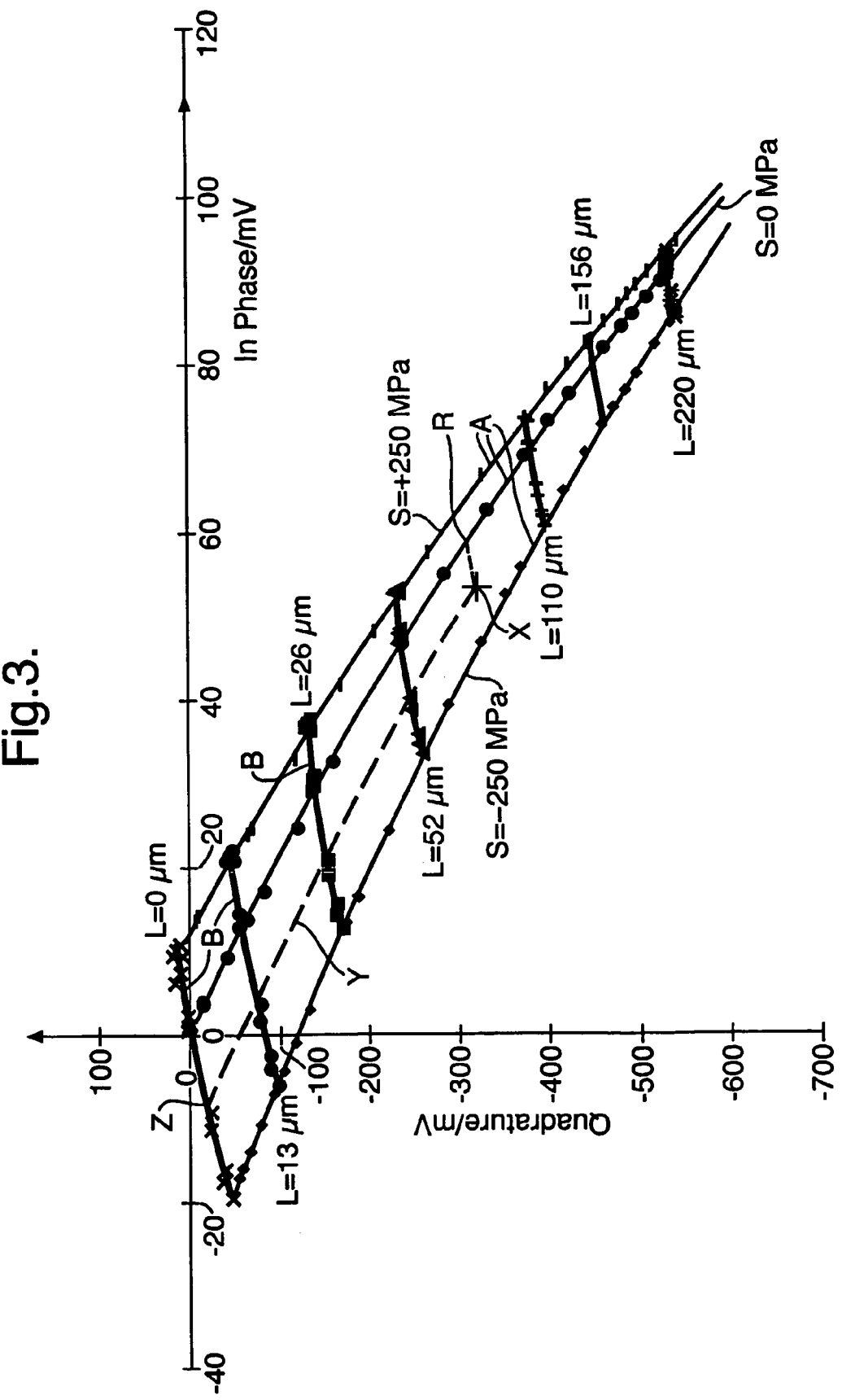
FIG. 3 shows graphically the variation of the backed-off quadrature and in-phase components of the flux linkage signal with variations of lift-off, and with variations of stress.

The values of the stresses in the directions of the principal stress axes can be determined from the experimental measurements of the flux linkage signals with the probe 12 oriented in those directions. This requires calibration of the apparatus 10, taking measurements on a sample of material of the same type as that of the object 16, while subjecting it to a variety of different stresses. This may be done with a rectangular strip sample in a test rig, measurements being made at the centre of the sample where the principal stress direction is aligned with the axis of the test rig. Referring to FIG. 3 this shows the backed-off flux linkage in-phase and quadrature components obtained in such a test rig, the measurements being made with a drive frequency of 70 Hz, and the specimen being a steel bar. A first set of measurements were made at progressively larger values of lift-off, L, but with no stress, S. This gives the lift-off line or contour A, the lift-off varying between 0 and 220 µm. Similar lift-off lines A are obtained for other fixed values of stress, those for S=250 MPa tension and compression being shown. Measurements were then made at a range of different fixed values of lift-off, L, with varying stresses, S (both compression and tension), providing the contours B.

It will be appreciated that the contours A are curved, and the contours B are not orthogonal to the contours A, but that they intersect at angles that are constant along any one lift-off line A. Consequently it is only necessary to make calibration measurements sufficient to plot one such contour B and two or three such contours A, and the shapes of the other contours can be predicted. It has also been found that the intersection angles, and the curvature of the contours, are characteristic of the material.

After calibrating the probe 12 in this manner, measurements of stress or of lift-off can be readily made from observations of flux linkage signals (resolved and backed off), as the contours enable the changes due to lift-off to be readily distinguished from changes due to stress. Any particular position in the impedance plane (i.e. in the graph of quadrature against in-phase components) corresponds to a particular value of stress and a particular value of lift-off. The mapping between (in-phase, quadrature) coordinates and (stress, lift-off) coordinates may be carried out graphically, referring to such contours, or by calculation. For example if the flux linkage signal has the in-phase and quadrature components of the position marked X, this corresponds to a lift-off of about 80 µm and a stress of about −125 MPa. Alternatively the value X may be translated along a contour B of constant lift-off to find the two components (at position R) for zero stress, and so to find the lift-off. Similarly this value X may be translated (along the broken line Y) along a contour A of constant stress to find the in-phase and quadrature components at position Z for zero lift-off.

Determination of the positions R and Z may be carried out graphically, as shown in the figure. Another method is to deduce theoretical equations for how the signal will vary with lift-off and material properties, taking into account the reluctance of the three parts of the magnetic circuit: the U-core 26, the air gaps, and the magnetic path through the object 16. To provide an accurate fit to the experimental data, it would be desirable also to take into account any losses in the core 26 and hysteresis losses in the object 16, and also flux leakage. Alternatively, simple polynomials may be used to model the experimental measurements; although this approach provides little insight into the physical phenomena it has been found to be the most accurate approach. This latter approach may be modified, based on the experimental observation that the intersection angles along any lift-off line and a set of stress lines remains constant.

The contours of constant stress, σ (referred to as lift-off lines) and contours of constant lift-off, L (referred to as material or stress lines) constitute a non-linear two-dimensional matrix on the impedance plane. The requirement is to determine for any subsequent impedance measurement the independent vector lengths on the impedance plane corresponding to a change in material and a change in lift-off. That is to say, the measurement, $(x_m, y_m)$ corresponding to the position X must be separated into the two specific components $(x'_o, y'_o)$ at position Z, and $(x'_L, y'_L)$ at position R, where these two components must lie on the zero lift-off stress line and the zero stress lift-off line respectively.

This analysis may be achieved in the following stages:

(A) General analysis for the lift-off/stress matrix measurements (1) The lift-off/stress matrix is parameterised using simple polynomial equations. Typically this matrix may consist of between 3 and 5 lift-off lines and between 5 and 10 stress lines.

(2) All the intercepts between the lift-off and stress lines are then determined.

(3) Cubic fits are carried out for both in-phase and quadratic intercept values against the actual lift-off levels used when measuring the original stress lines (provided there are at least 4 measured stress lines).

(4) Stress lines can then be evaluated for any arbitrary lift-off using the cubic fit coefficients (provided there are at least 3 measured lift-off lines).

(B) Specific analysis for each subsequent measurement X (5) A new lift-off line is evaluated which passes exactly through the measurement point.

(6) The intersection, Z, of this new lift-off line with the zero lift-off stress line is determined, $(x'_o, y'_o)$.

(7) Find the stress line that passes exactly through the measurement point.

(8) The intersection, R, of this new stress line with the zero stress lift-off line is determined, $(x'_L, y'_L)$.

(9) Alternatively if stages (3) and (4) have been carried out then the new stress line can be compared to the cubic fit coefficients to determine the absolute lift-off level.

The above approach will now be described in greater detail, using the numbering of the steps given above.

(1) All the lift-off $(x_L, y_L)$ and stress $(x_\sigma, y_\sigma)$ lines are first fitted with quadratic equations:

$$y_L(\sigma) = a_L(\sigma) x_L^2 + b_L(\sigma) x_L + c_L(\sigma) \quad (1)$$

(where the coefficients are different for each different value of $\sigma$), and $$y_\sigma(L) = a_\sigma(L) x_\sigma^2 + b_\sigma(L) x_\sigma + c_\sigma(L) \quad (2)$$

(where the coefficients are different for each different value of lift-off)

It can be useful to evaluate the intersection angle between the lift-off and stress lines, $\gamma$, at an arbitrary intersection position $(x', y')$:

$$\tan\gamma = \frac{2(a_L(\sigma) - a_\sigma(L))x' + (b_L(\sigma) - b_\sigma(L))}{1 + (2a_\sigma(L)x' + b_\sigma(L))(2a_L(\sigma)x' + b_L(\sigma))} \quad (3)$$

For the lift-off lines we shall specifically identify the most extreme cases that mark the edges of the matrix, for example those for compressive and tensile stresses of 250 MPa in the figure.

$$y_L(\sigma_c) = a_L(\sigma_c)x_L^2 + b_L(\sigma_c)x_L + c_L(\sigma_c) \quad (4)$$

where $\sigma_c$ is always the largest compression, and $$y_L(\sigma_t) = a_L(\sigma_t)x_L^2 + b_L(\sigma_t)x_L + c_L(\sigma_t) \quad (5)$$

where $\sigma_t$ is the largest tensile stress (or at any rate the tensile stress giving the largest difference in signal from that at zero stress). Also the lift-off line measured at zero applied stress, $$y_L(0) = a_L(0)x_L^2 + b_L(0)x_L + c_L(0) \quad (6)$$

For the stress lines we shall identify the one at zero lift-off, $$y_\sigma(0) = a_\sigma(0)x_\sigma^2 + b_\sigma(0)x_\sigma + c_\sigma(0) \quad (7)$$

(2) The intercepts between measured lift-off and stress lines are determined by setting $(x_L, y_L)$ and $(x_\sigma, y_\sigma)$ equal to $(x_{\sigma L}, y_{\sigma L})$ in equations (1) and (2), and solving using the fitted polynomial coefficients:

$$x_{\sigma L} = \frac{(b_\sigma(L) - b_L(\sigma)) \pm \sqrt{(b_L(\sigma) - b_\sigma(L))^2 - 4(a_\sigma(L) - a_L(\sigma))(c_\sigma(L) - c_L(\sigma))}}{2(a_\sigma(L) - a_L(\sigma))} \quad (8)$$

then $y_{\sigma L}$ from (1) or (2). (9)

Care must be taken to select the solution of equation (8) which lies within the bounds of the lift-off/stress matrix.

(3) The intercepts, $(x_{\sigma L}, y_{\sigma L})$, along each lift-off line are fitted to cubic equations to parameterise the true lift-off values using the 5 to 10 experimental lift-off values.

$$x_{\sigma L} = p_x(\sigma)L^3 + q_x(\sigma)L^2 + r_x(\sigma)L + s_x(\sigma) \quad (10)$$

$$y_{\sigma L} = p_y(\sigma)L^3 + q_y(\sigma)L^2 + r_y(\sigma)L + s_y(\sigma) \quad (11)$$

where the two sets of coefficients p, q and r for x and y are numbers that are different for each value of stress (three in this example).

(4) A general complete set of stress lines can then be determined using the coefficients in equations (10) and (11) for all lift-offs within the measurement range and for small extrapolations beyond that range. I.e. evaluate general $(x_{\sigma L}, y_{\sigma L})$ using equations (10) and (11) for each measured lift-off line, then for each lift-off, L=L', collect all intercepts $(x_{\sigma L}', y_{\sigma L}')$ and fit quadratics to these as in equation (2) but now we have generated stress lines for all specified lift-off values, these lines making smooth transitions between the measured stress lines.

(B) Specific analysis for each measurement on component or plant.

(5) For a measurement $(x_m, y_m)$, the lift-off line which passes directly through it can be expressed as (referring to equations (4)–(6)):

$$y_L = [a_L(0) + \Delta(a_L(\sigma_t) - a_L(\sigma_c))]x_L^2 + [b_L(0) + \Delta(b_L(\sigma_t) - b_L(\sigma_c))]x_L + [c_L(0) + \Delta(c_L(\sigma_t) - c_L(\sigma_c))] \quad (12)$$

where the parameter, $\Delta$, represents the relative position across the lift-off/stress matrix along the stress lines, and is given by:

$$\Delta = \frac{y_m - a_L(0)x_m^2 - b_L(0)x_m - c_L(0)}{[(a_L(\sigma_t) - a_L(\sigma_c))x_m^2 + (b_L(\sigma_t) - b_L(\sigma_c))x_m + (c_L(\sigma_t) - c_L(\sigma_c))]} \quad (13)$$

In equation (12) the expressions within square brackets are numerical coefficients, say $A_1$, $B_1$ and $C_1$. This parameter $\Delta$ effectively subdivides the area where there are contours, giving equally spaced lift-off lines with a smooth variation, based on just three measured lift-off lines. Note that this analysis does not use the information determined in steps (2), (3), or (4) above.

(6) The intersection of the specific lift-off line (12) with the zero lift-off stress line, (7), $(x'_\sigma, y'_\sigma)$, is given by:

$$x'_\sigma = \frac{(b_\sigma(0) - B_1) \pm \sqrt{(B_1 - b_\sigma(0))^2 - 4(a_\sigma(0) - A_1)(c_\sigma(0) - C_1)}}{2(a_\sigma(0) - A_1)} \quad (14)$$

then $y'_\sigma$ from equation (7) by substitution. (15)

Here again care must be taken to select the correct solution.

(7–9) Find the stress line that passes exactly through the measurement point. In step (4) above, all general stress lines (and their coefficients) were determined. Therefore it is only necessary to determine which line includes the measurement point, $(x_m, y_m)$. There are several ways to do this, one being to determine the shortest distance, D, from the point to each stress line:

$$D(L) = \sqrt{(x_m - x^*_\sigma(L))^2 + (y_m - y^*_\sigma(L))^2} \quad (16)$$

where the $(x^*_\sigma, y^*_\sigma)$ are the closest corresponding positions on each stress line given by the solution to the simultaneous equations:

$$y^*_\sigma(L) - y_m = \frac{x_m - x^*_\sigma(L)}{2a_\sigma(L)x^*_\sigma(L) + b_\sigma(L)} \quad (17)$$

$$(2a_\sigma(L)x_\sigma^*(L) + b_\sigma(L))(a_\sigma(L)x_\sigma^{*2}(L) + b_\sigma(L)x_\sigma^*(L) + c_\sigma(L) - y_m) + (x_\sigma^*(L) - x_m) = 0 \quad (18)$$

Thus for the range of L we find $D(L)|_{min}$ and so determine the absolute lift-off, L, for the measurement.

An advantage of this method, using stress lines determined using the coefficients in equations (10) and (11) for all different values of lift-off (as outlined in step (4) above), is that it makes use of data from all the different experimentally-determined stress lines (of which there are seven shown in the figure, from L=0 to L=220 μm).

Alternatively if absolute lift-off value are not used and stages (3) and (4) have not been carried out, then by working with polynomial intersections in a manner analogous to that for the lift-off lines, the intersection point R can be obtained.

An alternative analysis approach takes into account the experimental observation of a constant intersection angle, γ, along each lift-off line, in determining the equations of the lift-off lines and stress lines. The result is more robust to extrapolation beyond the calibrated lift-off range and requires fewer measurements of stress and lift-off lines to construct.

The measured lift-off lines are fitted with simple quadratic equations as described by equations (4) to (7). These are typically taken so as to represent the two extreme values of stress and the zero stress lift-off line respectively (three lines, although more can be used). Only a single stress line needs to be measured, and this can be at any lift-off, $L_0$, equation (2). The intersection angles, $\gamma(\sigma)$, of the lift-off lines along the stress line are evaluated from equation (3). Let the tangent angle to any lift-off line be $\alpha_L(\sigma)$ and that to the stress line be $\beta_\sigma(L_0)$. Then:

$$\tan \alpha_L(\sigma) = 2a_L(\sigma)x_L + b_L(\sigma) \quad (19)$$

$$\tan \beta_\sigma(L_0) = \tan(\alpha_L(\sigma) - \gamma(\sigma)) = \tan[\tan^{-1}(2a_L(\sigma)x_L + b_L(\sigma)) - \gamma(\sigma)] = 2a_\sigma(L_0)x_L + b_\sigma(L_0) \quad (20)$$

Expanding the more complicated tangent in equation (20):

$$\frac{2a_L(\sigma)x_L + b_L(\sigma) - \tan\gamma(\sigma)}{1 + (2a_L(\sigma)x_L + b_L(\sigma))\tan\gamma(\sigma)} = 2a_\sigma(L_0)x_L + b_\sigma(L_0) \quad (21)$$

In equation (21) all the polynomial coefficients and the gamma angles are already known. However we know that $\gamma(\sigma)$ is independent of the lift-off, and so we can generalise equation (21) to all lift-off values, L:

$$\frac{2a_L(\sigma)x_L + b_L(\sigma) - \tan\gamma(\sigma)}{1 + (2a_L(\sigma)x_L + b_L(\sigma))\tan\gamma(\sigma)} = 2a_\sigma(L)x_L + b_\sigma(L) \quad (22)$$

where now the stress line coefficients and the intercept between this line and any lift-off line (RHS of equation (22)) must be established.

To do this we simply solve the simultaneous equations (22) using coefficients from 2 or 3 lift-off lines together with equations (2), (4), (5) and (6) to determine the stress line coefficients and intercept positions. Note that any x position, $x_L$, can be chosen on a lift-off line and the corresponding y position and stress line coefficients determined for that case.

Hence the position Z can be determined, eliminating the effect of any lift-off, and this can be related to stress. The value of stress found in this way is, it will be appreciated, the uniaxial stress that would provide that value of the flux linkage signal. If the stresses are actually biaxial, then a further calibration must be carried out with a cross-shaped sample in a test rig, flux linkage signal measurements being made at the centre of the sample where the principal stress directions are aligned with the axes of the test rig. Hence a graph or map may be obtained for a range of values of stress on one principal axis (say the x-axis) and for a range of values of stress in the other principal axis (say the y-axis), with contours each of which shows the values of biaxial stress that give a particular value of apparent uniaxial stress along the x-axis; and a similar map may be obtained with contours showing values of biaxial stress that give a particular value of apparent uniaxial stress along the y-axis. Hence from measurements of apparent uniaxial stress along the two principal stress axes obtained as described earlier, the biaxial stress can be determined.

It will again be appreciated that the biaxial stress may be determined either graphically or by calculation in this way. Apparent values of uniaxial stress (in MPa) may be used for this purpose, or alternatively the numerical value of the flux linkage signal (in mV), either the in-phase or quadrature value, obtained by eliminating the effect of lift-off as described in relation to FIG. 3, may be used.

For some materials, such as hard steel, the biaxial stress contours for different values of apparent uniaxial stress (or of flux linkage signal) along the x-axis, and those along the y-axis, intersect at large angles over the entire biaxial stress plane. Finding the intersection of two such contours, and so the true value of the biaxial stress, can be done easily. However for mild steel the two sets of contours (particularly in the tensile/tensile quadrant) are almost parallel, so it is very difficult to locate their intersection. In this case measurements with a different stress-dependent variable are helpful, as they can provide a third set of contours; the flux rotation signals are desirably used for this purpose.

It will be appreciated that the invention enables lift-off to be distinguished from changes in material properties (such as stress), over a wide range of values of both lift-off and material properties, as it does not require an assumption that the changes are linear in the impedance plane. The probe described above is just one type of electromagnetic probe for which the invention is applicable. The electromagnet means may include a ferromagnetic core on which a drive coil is wound, such as a C-core or a rod, or may be air cored. The sensor may be a sensing coil wound on the same core, or a sensing coil positioned near to a pole, or may indeed be the same coil as the drive coil. There may also be several sensor coils, for example in an array.

Measurements of lift-off require at least a region of surface on which there is no coating, either on the object 16 or on a test piece of the same material, so that a measurement at zero lift-off can be made. Subsequently the thickness of any coating of non-ferromagnetic material can be measured, as it is equal to the lift-off if the probe is in contact with the coating. As a rule, a probe smaller than that described above would be more sensitive to lift-off and less sensitive to material properties, so that if the primary intention is to measure lift-off then a probe of external diameter say 8 mm or 4 mm might be used. The shape of a surface, for example any undulations in the upper surface of a rail head, may therefore be measured in a non-contact fashion by scanning a single probe over the surface and monitoring the changes of lift-off determined as described above; alternatively an array of probes might be used for this purpose, and might also be scanned in this fashion. When taking measurements on a surface that is curved, it is desirable for the face of the probe to have a similar curvature.

It will thus be appreciated that the present invention is particularly suited to the determination of stress in a ferromagnetic material, as changes in stress have a large effect on the relative permeability, $\mu_r$, while having a negligible effect on conductivity. A single specimen can be used for generating the signal/stress data and the stress/lift-off data, by subjecting the specimen to a range of different uniaxial or biaxial stresses. The resulting data can subsequently be used in taking measurements on many different objects of the same type of material. In general there is a need to determine three independent parameters—the direction of the principal axes, and the stresses along each principal axis. It is hence desirable, in general, to take measurements with different orientations of the probe.

The invention claimed is:

1. A method for measuring biaxial stresses in an object of ferromagnetic material, said method comprising the steps of using at least one probe, the, or each, probe comprising an electromagnet means and a magnetic sensor arranged for sensing a magnetic field due to said electromagnet means, the method for the, or each, probe comprising arranging the probe adjacent to said object, and activating the electromagnet means for generating an alternating magnetic field in said electromagnet means and consequently in said object, the generated magnetic field alternating at a frequency selected for providing a desired depth of penetration below a surface of said object; detecting signals from said magnetic sensor and resolving said signals into an in-phase component and a quadrature component which are orthogonal in phase, and mapping said in-phase and quadrature components directly into apparent stress and lift-off components by means of a first calibration, using a sample of said ferromagnetic material and subjecting said sample to a range of different uniaxial stresses with one said probe at a range of different values of lift-off for deducing corresponding curved contours in a graph of quadrature against in-phase components; arranging the one said probe adjacent to the ferromagnetic object, turning the one said probe to different orientations and detecting signals from said magnetic sensor when the one said probe is oriented with two principal stress axes thereof, and then from the curved contours deduced in the first calibration deducing two corresponding values of apparent uniaxial stresses along said two principal stress axes; and, by means of a second calibration with a sample of the ferromagnetic material subjected to a range of different biaxial stresses, deducing the true biaxial stress in said object from the two values of apparent uniaxial stress.

2. A method as claimed in claim 1 wherein said electromagnetic means comprises an electromagnetic core and two spaced apart electromagnetic poles, and said magnetic sensor is arranged for sensing the reluctance of that part of the magnetic circuit between the poles of said electromagnet means.

3. A method as claimed in claim 1 wherein said contours deduced in the first calibration are represented by polynomials for performing said mapping.

4. A method for measuring biaxial stresses in an object of ferromagnetic material, said method comprising the steps of using at least one probe, the, or each, probe comprising an electromagnet means and a magnetic sensor arranged for sensing a magnetic field due to said electromagnet means, the method for the, or each, probe comprising arranging the probe adjacent to said object, and activating the electromagnet means for generating an alternating magnetic field in said electromagnet means and consequently in said object, the generated magnetic field alternating at a frequency selected for providing a desired depth of penetration below a surface of said object; detecting signals from said magnetic sensor and resolving said signals into an in-phase component and a quadrature component which are orthogonal in phase, and mapping said in-phase and quadrature components directly into apparent stress and lift-off components by means of a first calibration, using a sample of said ferromagnetic material and subjecting said sample to a range of different uniaxial stresses with one said probe at a range of different values of lift-off for deducing corresponding curved contours in a graph of quadrature against in-phase components; arranging the one said probe adjacent to the ferromagnetic object, turning the one said probe to different orientations and detecting signals from said magnetic sensor when the one said probe is oriented with two principal stress axes thereof, and then from the curved contours deduced in the first calibration deducing two corresponding values of apparent uniaxial stresses along said two principal stress axes; and, by means of a second calibration with a sample of the ferromagnetic material subjected to a range of different biaxial stresses, deducing the true biaxial stress in said object from the two values of apparent uniaxial stress, wherein the second calibration entails measuring a set of contours each of which shows the values of biaxial stresses that give a particular value of apparent uniaxial stress along one principal stress axis, and a second set of contours each of which shows the values of biaxial stresses that give a particular value of apparent uniaxial stress along the other principal stress axis.

5. A method for measuring biaxial stresses in an object of ferromagnetic material, said method comprising the steps of using at least one probe, the, or each, probe comprising an electromagnet means and a magnetic sensor arranged for sensing a magnetic field due to the electromagnet means, the method for the, or each, probe comprising arranging the probe adjacent to said object, and activating said electromagnet means for generating an alternating magnetic field in said electromagnet means and consequently in said object, the generated magnetic field alternating at a frequency selected for providing a desired depth of penetration below a surface of said object; detecting signals from magnetic sensor and resolving said signals into an in-phase component and a quadrature component which are orthogonal in phase, and mapping said in-phase and quadrature components directly into apparent stress and lift-off components by means of a first calibration, using a sample of said ferromagnetic material and subjecting said sample to a range of different uniaxial stresses with one said probe at a range of different values of lift-off for deducing corresponding curved contours in a graph of quadrature against in-phase components; arranging said one probe adjacent to the ferromagnetic object, turning said one probe to different orientations for detecting signals from said magnetic sensor when said one probe is oriented with the two principal stress axes, and from said curved contours deduced in the first calibration deducing two corresponding values of apparent uniaxial stresses along the two principal stress axes; and, performing a second calibration with a sample of said ferromagnetic material subjected to a range of different biaxial stresses, for deducing the true biaxial stress in said s object from the two values of apparent uniaxial stress wherein the contours deduced in the first calibration are represented by polynomials for performing said mapping, a constant intersection angle along a contour representing signal variation with lift-off being taken into account in generating said polynomials.

* * * * *